United States Patent [19]

Pennock

[11] Patent Number: 4,960,118
[45] Date of Patent: Oct. 2, 1990

[54] METHOD AND APPARATUS FOR MEASURING RESPIRATORY FLOW

[76] Inventor: Bernard E. Pennock, 405 Wickford Dr., Pittsburgh, Pa. 15238

[21] Appl. No.: 345,568

[22] Filed: May 1, 1989

[51] Int. Cl.$^5$ .................................. A61M 16/00
[52] U.S. Cl. ........................... 128/200.24; 128/721
[58] Field of Search ............... 128/200.24, 204.23, 128/898, 716, 720–721, 723–725; 137/908; 116/264

[56] References Cited

U.S. PATENT DOCUMENTS

| | | | |
|---|---|---|---|
| 3,483,861 | 12/1969 | Tiep | 128/721 |
| 3,782,368 | 1/1974 | Rebold | 128/721 |
| 4,267,845 | 5/1981 | Robertson, Jr. et al. | 128/725 |
| 4,308,872 | 1/1982 | Watson et al. | 128/725 |
| 4,373,534 | 2/1983 | Watson | 128/721 |
| 4,452,252 | 6/1984 | Sackner | 128/721 |
| 4,456,015 | 6/1984 | Sackner | 128/721 |
| 4,576,179 | 3/1986 | Manus et al. | 128/721 |
| 4,817,625 | 4/1989 | Miles | 128/725 |
| 4,834,109 | 5/1989 | Watson | 128/721 |

FOREIGN PATENT DOCUMENTS

| | | | |
|---|---|---|---|
| 2181555 | 4/1987 | United Kingdom | 128/721 |
| 2194343 | 7/1987 | United Kingdom | 128/721 |

OTHER PUBLICATIONS

"The Impedance Pneumograph" Aerospace Medicine Jan., 962 pp. 28–33.

Primary Examiner—Eugene H. Eickholt
Attorney, Agent, or Firm—Webb, Burden, Ziesenheim & Webb

[57] ABSTRACT

A method and apparatus for accurately measuring respiratory flow, while the subject breathes, without using a mouthpiece, face mask or any device about the head. The rate of change of the circumference of the rib cage (chest) and the rate of change of the circumference of the abdomen are measured using an extensible belt with series strips of piezoelectric film. The stress on the film produces an electric output proportional to the rate of application of stress when connected to a proper electronic amplifier. Calibration is performed by measuring the circumference changes while the subject performs an isovolume maneuver for several breaths or while the subject breathes through a pneumotachometer and mouthpiece at a variable rate for several breaths.

9 Claims, 7 Drawing Sheets

METHOD AND APPARATUS FOR MEASURING RESPIRATORY FLOW

This invention relates to a method and device to measure respiratory flow using piezoelectric film-elastic belts around the rib cage and abdomen.

BACKGROUND OF THE INVENTION

In medical diagnosis and in physiologic evaluation it is desirable to precisely quantitate respiratory flow over time. The usual methods employ a mouthpiece or a mask. These devices are not always tolerated by subjects (or patients) and even if tolerated, they interfere with respiration, the very parameter being measured. In addition, mouthpieces and masks limit freedom of movement, are inconvenient and uncomfortable, particularly when used over extended times.

These problems have been overcome by quantitating respiratory volume changes by measuring the movement of the rib cage and abdomen as a reflection of changes in lung volume. Two pairs of magnetometers have been placed on the surface of the rib cage and abdomen to quantitate anterior-posterior distance change. The magnetometer pairs produce a voltage proportional to their separation.

In addition a technique has been described that measures the movement of the rib cage and abdomen using insulated wire, held closely encircling the torso, whose inductance changes are proportional to the cross sectional area enclosed. This variable inductance is connected to a variable frequency LC oscillator which is in turn connected to a frequency to voltage convertor giving a voltage proportional to cross sectional area of the torso.

In both of these techniques the two voltages (from rib cage and abdomen) must be calibrated, i.e., they are properly weighted and summed to give a voltage proportional to instantaneous lung volume. The mathematical formulation of the calibration is in both instances based on the publication of Konno and Mead.

To measure rib cage or abdominal expansion, a moment actuated piezoelectric crystal pulled by an elastic belt worn around the chest or abdomen has been described in Reibold, U.S. Pat. No. 3,782,368. Other devices including strain gauges, mercury filled silastic rubber, pneumatic tubes, and tissue electrical impedance have been used. All of these devices are qualitative relative to actual dimension change. They either fail to be linear or fail to follow dimensional changes instantaneously.

The magnetometer technique requires bulky apparatus and undesirable limitation on the activity and movement of the subject. The inductance technique has a limited response time. It is further limited by the sensitivity of the LC oscillator to electric connection. The sensitivity of calibration is limited by movement of the inductance wire on the torso.

The Reibold moment piezoelectric crystal fails to provide means for a quantitative measurement. It is sensitive to position around the body and to distortion of the elastic belt. It requires significant limitation on the activity and movement of the subject, e.g., turning in bed. Finally, baseline drift requires predetermined and constant static belt tension.

SUMMARY OF THE INVENTION

The shortcomings in prior measurement techniques are solved by using two elastic belts with series piezoelectric film strips to measure circumference changes in the rib cage and abdomen. The belts are comfortable and can be applied about a subject in seconds. Their output voltage follows stress on the film without measurable phase shift at least to $5H_z$. The subject may move about freely within the limitation of attached wires. (This limitation can be eliminated by attaching the amplifier and a transmitting device directly on the belt.) The calibration values are less sensitive to sliding of the belts than is the case with the wire inductance.

Many problems with the prior art have been solved with the piezoelectric film belts. The complex, position sensitive moment-actuated piezoelectric crystal is replaced by a directly stressed flat film. A durable connection technique capable of withstanding large shear tension on the film caused by accident or motion expansion of the chest or abdomen has been developed. Electrical connections that resist film tearing associated with mechanical stress have been developed.

A system for mounting multiple series sensors to prevent loss of signal associated with external interferences such as covering by arm or rolling over during sleep has been developed. Sensors can be easily removed so that the elastic belts can be laundered.

The electric output is quantitative (linear and without phase shift) relative to the rate of change of the chest or abdomen, i.e., quantitative flow signal. There is no baseline drift and static tension is noncritical. There is circumferential homogeneity, i.e., a sensor on the front and back of the belt give identical signals.

DETAILED DESCRIPTION OF THE INVENTION

Figure 1:
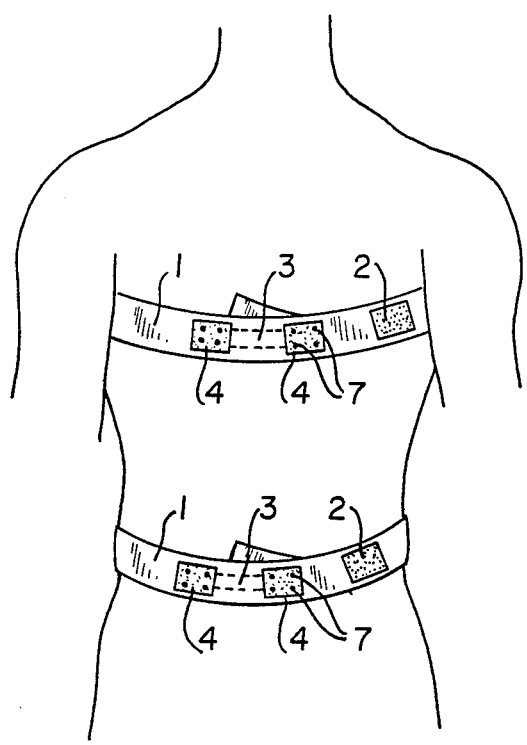
FIG. 1 shows the two elastic belts in place about the subject's rib cage and abdomen.

The basis of the device is the stretch belts, constructed with a series piezoelectric film which produces a voltage proportional to the rate of change of the torso circumference. The belts are placed about the rib cage and the abdomen as shown in FIG. 1. The use of two belts is predicated on the behavior of the respiratory system as a two degree of freedom system as described by Konno and Mead (*J. App. Physiol.*, 22:407–422, (1967)). Direct differentiation of their equations describe the system in terms of flow instead of volume.

The construction of the belts is such, however, that the motion of other dimensions could be conveniently measured and their use is by no means limited to two degrees of freedom. Examples of this extension include, for example, a third degree of freedom measuring motion of the dimension between umbilicus and sternum as described by Smith and Mead (*J. App. Physiol.*, 60:928-934, (1986)), or multiple belts around the torso filling in the spaces between the previously described rib cage and abdominal belt.

BELTS

Figure 1A:
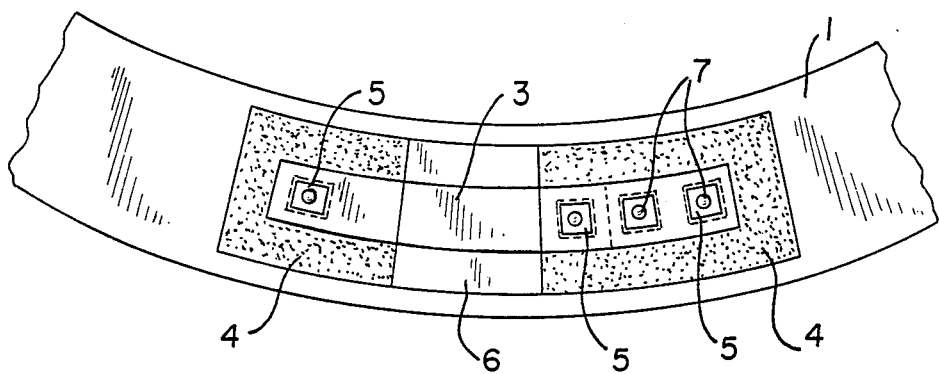
FIG. 1A is an expanded view showing the attachment of the piezoelectric film to the stretchable Velcro ® belt.

FIG. 1 and FIG. 1A show the construction of the respiratory belt. The stretchable Velcro ® (loops) band 1 encircles the torso and is attached by the Velcro ® (hooks) tab 2 on the end of the belt. The belt thus is of adjustable length from its maximum length to a shortest length of the distance from one end to the piezoelectric film 3. The piezoelectric film 3 is polyvinylidene flouride chloride (Kynar) manufactured by Pennwalt Corporation. In the preferred embodiment of the present invention this film is 52μ thick, 22 mm wide and 8 cm long and is coated with a silver ink for metallic contact. The thickness, length and width are not critical for qualitative operation but do change the voltage response characteristics.

The Kynar film 3 is sandwiched between adhesive Velcro ® hooks 4 on each end. The sandwich of Velcro ® is crimp (plastic) riveted 5 for mechanical strength. Lycra ® is sewn to the short Velcro ® strips as a protective cover 6 for the Kynar film. Electrical connections are made with metal washers and rivets 7.

Whenever rivets are passed through the film it is necessary to remove the metallic coating from one side of the pass through hole to prevent electrical shorting of one side of the film to the other. The metallic coating must still, however, provide a path for electrical conduction along the long dimension of each side of the film. The rivets and washers provide a large contact surface area to prevent film tearing at the pass through hole.

Figure 1B:
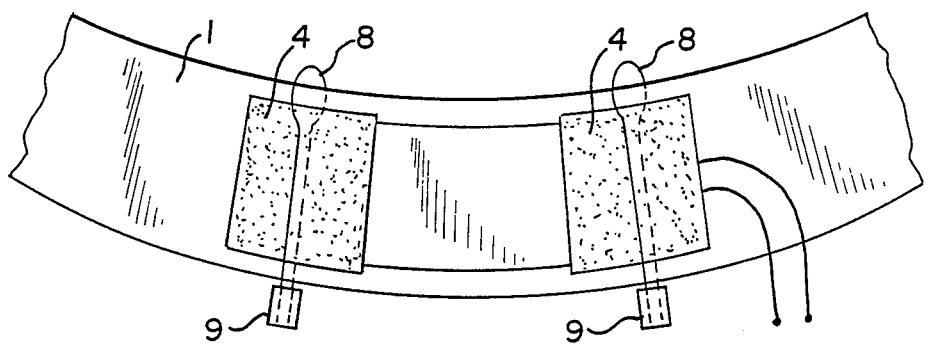
FIG. 1B shows the attachment of the strip to the stretchable Velcro ® belt.
Figure 1C:
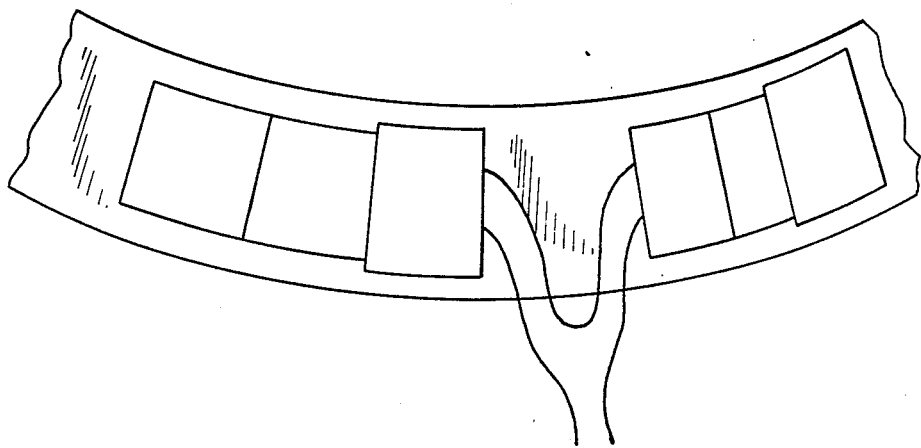
FIG. 1C shows a scuba vest.

These short sensor strips are fastened (and can be removed and repositioned) to the stretch Velcro ® as shown in FIG. 1B. The connection between the hooks and loops is reenforced with spring clips 8 and rubber bands 9. These prevent sliding of the hooks and loops under shear stress. The use of removable sensors allows easy placement and use of multiple sensors on one belt. This is useful, for example, in a subject lying in bed, who by a change in position mechanically blunts the response of one sensor. The other will, if positioned properly, allow continued operation. The sensors in the configuration are connected electrically in series as shown in FIG. 1C.

Figure 1D:
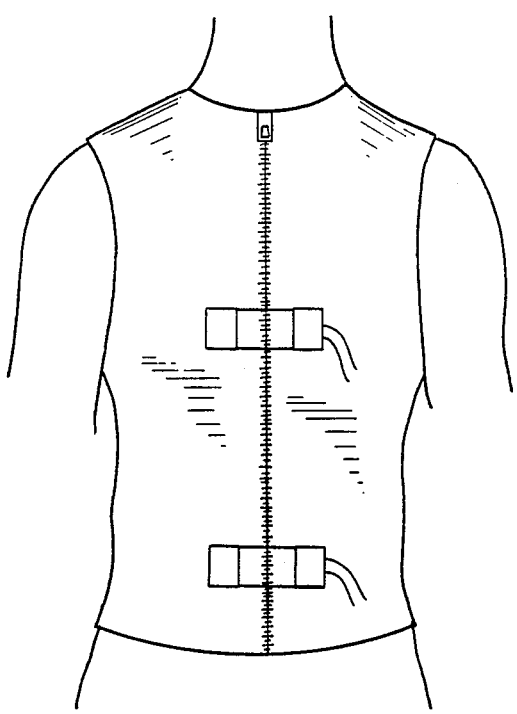
FIG. 1D shows a series connection of sensors.

Another alternative design for application of the belts is illustrated in FIG. 1D. Instead of the stretchable Velcro ® belts, Velcro ® strips are placed on a vest made of ¼ inch neoprene rubber, a scuba wet suit vest 10. The sensor strips shown in FIG. 1A are then attached to the vest at these Velcro ® fasteners 1.

Figure 2:
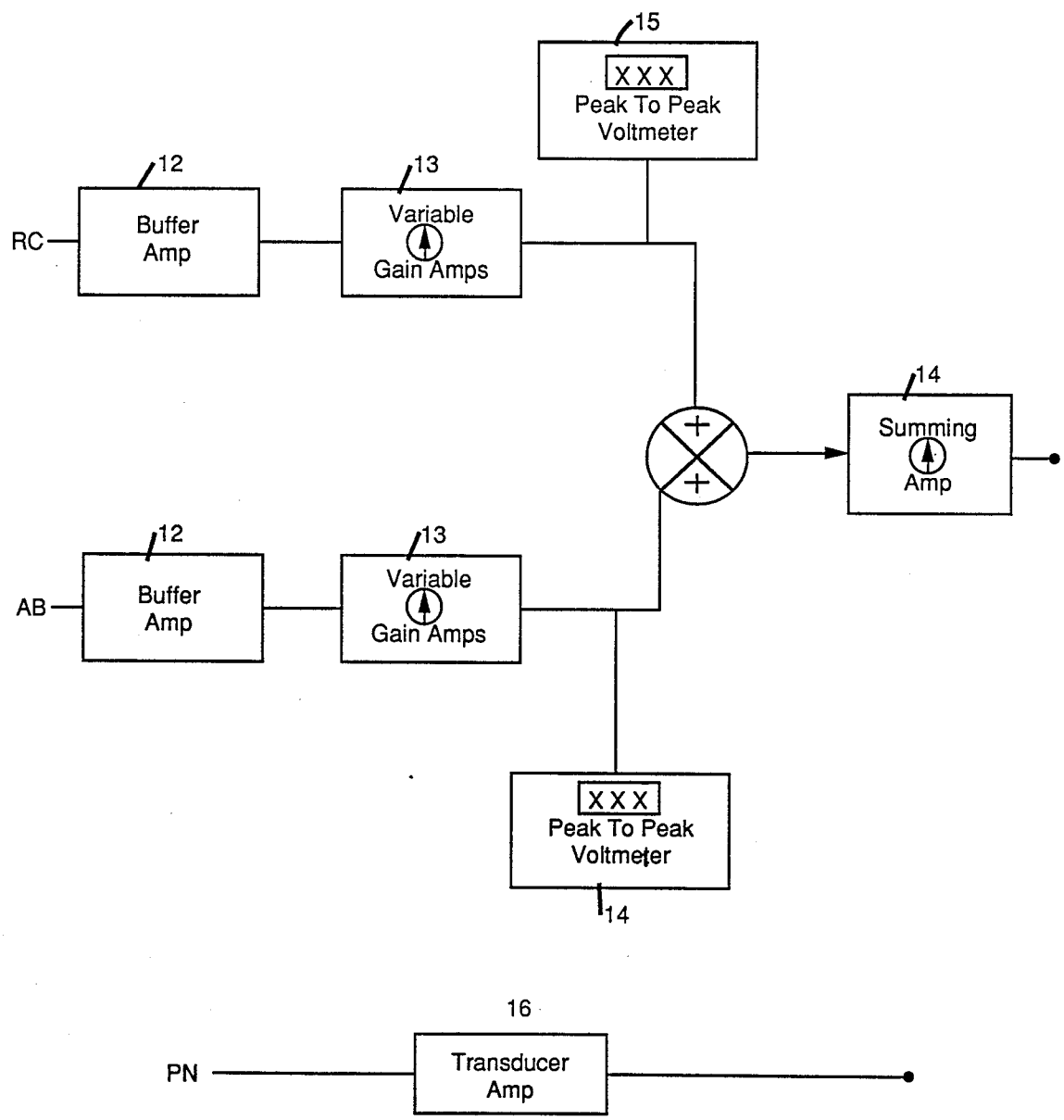
FIG. 2 is a block diagram of the apparatus for calibrating and proportional summing of the rib cage and abdominal signals to produce respiratory flow signal.

Having described the construction of the sensor belts, the electronic processing of the voltage signals will be described. FIG. 2 is a block diagram of the electronic part of the apparatus. The voltage generated by each belt is buffered by an amplifier 12 with input impedance of 1 MΩ and is amplified by a variable gain amplifier 13 and the outputs of the amplifiers are summed in another amplifier with variable gain 14. The averaged (2 seconds) peak-to-peak amplitude from each amplifier 13 is displayed on digital output voltage meters 15. A transducer amplifier 16 is included to be used to measure the pressure difference across a pneumotachometer during the calibration procedures.

Figure 3:
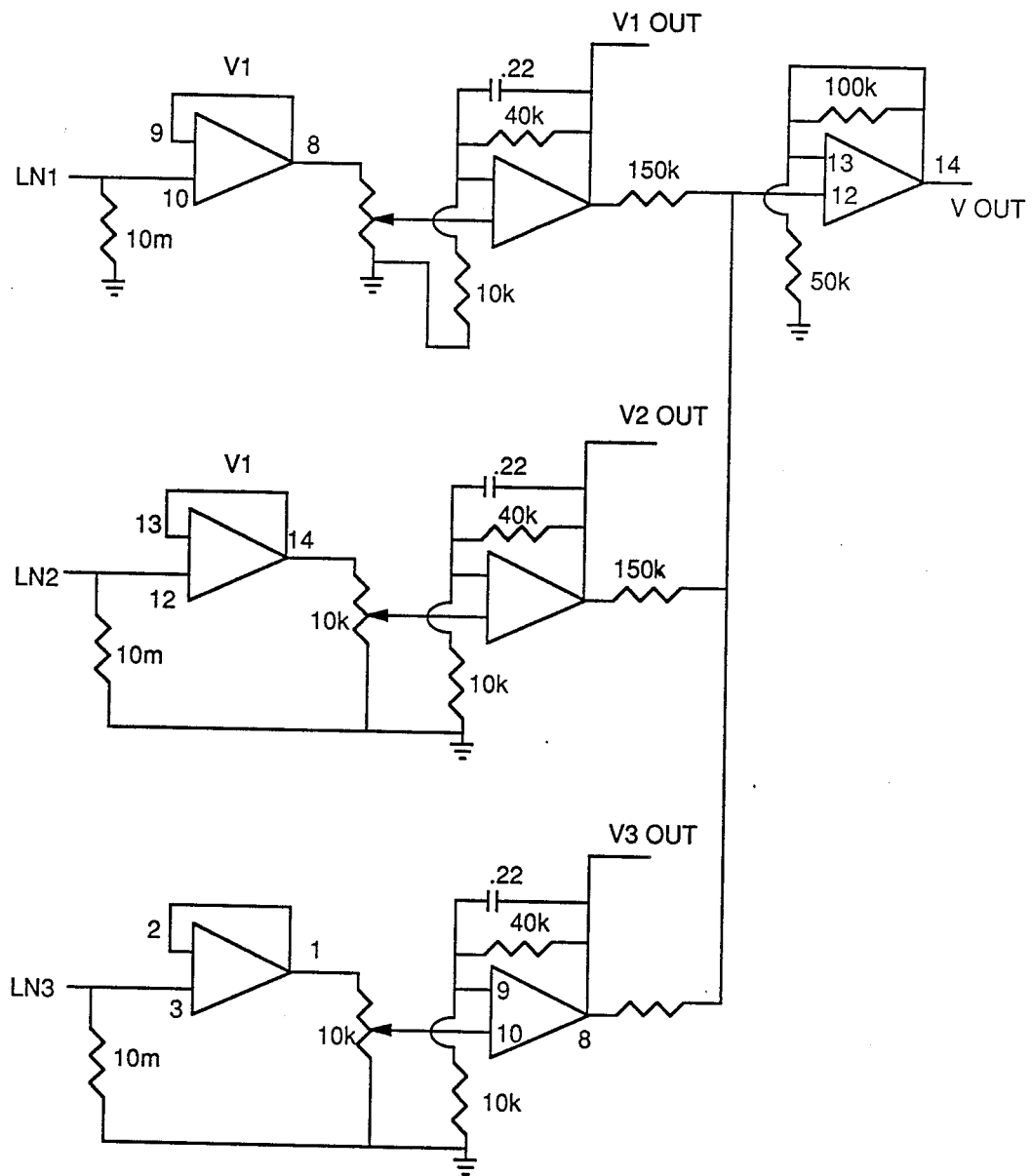
FIG. 3 is a detailed diagram of the components of FIG. 2.

The specific circuits used in the embodiment of this invention are shown in FIG. 3 These are standard circuits using operational amplifiers and alternative circuits could be designed to perform the same functions.

Calibration of the device will now be described. There are two steps to calibration. First, the relative gains of amplifiers 13 (FIG. 2) are set so that the flow of the summed signal always is proportional to the flow measured directly by a pneumotachometer. Secondly, the gain of the summing amplifier 14 is set so that the summed flow signal equals the pneumotachometer signal. It is the first of the two steps that requires a special procedure.

The preferred calibration procedure is as follows:

1. With the two belts in place (rib cage at the level just above the nipple and abdomen at the level of the 1-2 cm above the umbilicus) the subject performs an isovolume maneuver. The isovolume maneuver consists of the subject holding his breath and then causing slight gentle inward and outward motion of the abdomen. The effect of this maneuver is to shift air back and forth from the base to the apex of the lung. The maneuver is repeated for 6-10 breaths.

2. The envelope of the peak-to-peak voltage of the rib cage and abdomen are adjusted to be equal, with the gain controls of amplifiers 13. Since no air leaves the mouth, the flow leaving the base of the lung (abdomen) must be equal and opposite to the flow in the apex (rib cage). By adjusting the voltage outputs to be equal we have forced the voltages to be proportional to the separate actual flows.

Figure 4:
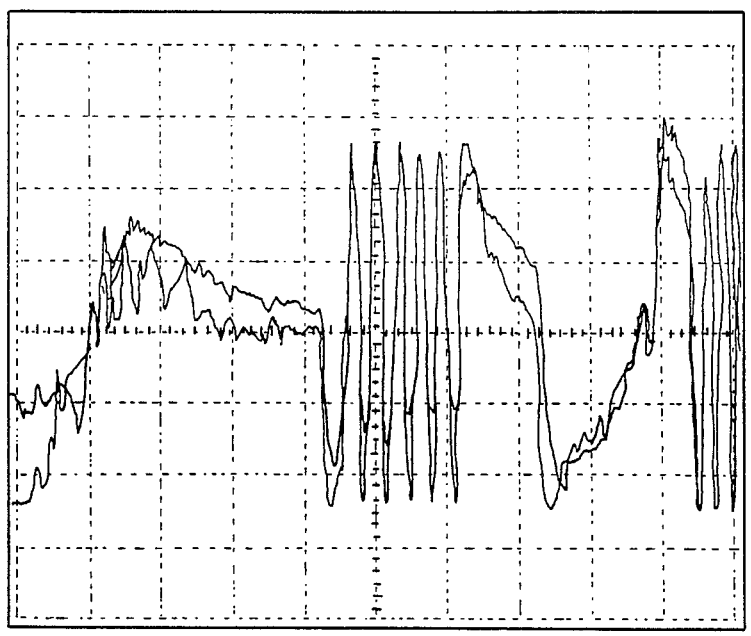
FIG. 4 is a tracing of respiratory flow obtained from the summation of signals from the belts compared to the signal from a screen pneumotachometer.

3. The gain of the summing amplifier 14 is adjusted so that its amplitude is equal to that of the previously calibrated pneumotachometer signal. FIG. 4 shows a comparison between flow measured with the invention and flow measured with a pneumotachometer.

An alternative calibration procedure is now described. It is particularly appropriate in the instance where the subject cannot perform the isovolume maneuver. This would, for example, apply for very sick or unconscious patients. This procedure can be described as a dynamic isovolume procedure. The subject must breathe through a pneumotachometer, preferably, but not necessarily at an ascending respiratory rate. The theory of the "dynamic isovolume" calibration is as follows. The two degrees of freedom respiratory system is described mathematically by $$\dot{V}_{PN} = A \dot{V}_{RC} + B \dot{V}_{AB}$$

where
$\dot{V}_{PN}$ is flow measured by pneumotachometer
$\dot{V}_{RC}$ is flow generated by rib cage belt
$\dot{V}_{AB}$ is flow generated by abdomen belt
A and B are unknown weighting factors
By algebraic manipulation this equation can be rewritten as:

$$\frac{B}{A} = \frac{\dot{V}_{PN}/\dot{V}_{AB}}{A} - \frac{\dot{V}_{RC}}{\dot{V}_{AB}}$$

When the actual flow $\dot{V}_{PN}$ approaches zero, and $\dot{V}_{RC}$ and $\dot{V}_{AB}$ do not, the ratio of weighting factors (or gains) becomes $$\frac{B}{A} = \frac{V_{RC}}{V_{AB}}$$

This equation states that the ratio of the gains of amplifiers 13 should be set to the value of the ratio of the rib cage and abdominal signals when there is zero pneumotachometer flow. $V_{RC}$ and $V_{AB}$ will be non-zero with zero respiratory flow when there is asynchrony between rib cage and abdominal excursions. This can be promoted in normal subjects by either loaded (increase in inspiratory resistance) or very rapid or very slow respiration. Asynchrony is very often a usual phenomenon in very sick patients, those very subjects who cannot perform the isovolume maneuver required in the preferred calibration technique.

The alternate calibration procedure is then as follows:

1. The gains in rib cage and abdominal amplifiers 13 are set to be equal by putting identical voltages into each channel and setting the outputs to be equal. The preferred method of measuring output is with an external chart recorder.

2. The subject breathes for 10–20 breaths through a pneumatachograph. Respiration must be asynchronous at times. This may occur naturally or be encouraged by loading breathing or high or low respiration rates.

3. At points of zero flow the ratio of $\dot{V}_{RC}$ to $\dot{V}_{AB}$ ($\dot{V}_{RC}/\dot{V}_{AB}$) is calculated ($\dot{V}_{RC}$ and $\dot{V}_{AB}$ cannot be zero).

4. The several values of the ratio are averaged and the gains of the two channels are adjusted using the identical source voltage inputs to give the calculated gain ratio. Now $A\dot{V}_{RC}$ will equal $B\dot{V}_{AB}$ in the isovolume procedure and the proportional contribution of rib cage and abdominal motion has been properly adjusted.

5. Same as step 3 in the preferred calibration procedure described previously.

Applications of this invention include those mentioned in U.S. Pats. No. 4,308,872, No. 4,452,252, and No. 4,456,015. In addition other specific applications include unencumbered measurement of ventilation.

1. in a sleeping subject.
2. in a subject undergoing artificial or mechanically driven external ventilation.
3. for synchronization of ventilation with magnetic resonance imaging.
4. in a smoking subject.
5. for examining patterns of respiration.
6. to describe rib cage—abdominal asynohrony of action.
7. to identify respiratory fatigue.
8. during indirect calorimetry using a hood.
9. to characterize respiratory muscle strength.
10. to examine flow-volume characteristics during resting/breathing.
11. to measure specific airway resistance.
12. as an alternate to a body plethysmograph in resistance and lung volume measurements techniques.
13. during speech.
14. during exercise.
15. all these application in animals.

Several applications in non-ventilatory areas include measurement of:

1. fetal activity in preterm pregnancy and immediately preceding and during labor (abdomen).
2. suprasternal notch motion (neck).
3. eye and eyelid motion (temple over eyes).
4. mechanical motion of the heart (in either abdominal or chest belt).
5. circulatory pulse (temple).
6. blood flow to the calf after release of arterial but not venous occlusion at the knee (calf).
7. muscle activity (tibia, thigh, forearm, biceps).

In all these applications the belt is wrapped around the body part of interest as indicated by description in parenthesis.

I have described a preferred and several alternate embodiments of the present invention. It is apparent that changes and modifications may be made without departing from the spirit and scope of the invention. The above description should be construed as illustrative and not in the limiting sense, the scope of the invention being defined by the following claims.

What is claimed is:

1. A method of measuring respiratory air flow comprising the steps of
   a. measuring the rate of change of abdomen circumference using an abdominal linear piezoelectric sensor, with said piezoelectric sensor being attached to an extensible abdominal belt by means of at least on non-electrically-conductive rivet, said linear piezoelectric sensor having an electrically-conductive coating on each side thereon, which coating on one side of said linear piezoelectric sensor is removed around said rivet, to provide an electrical output;
   b. measuring the rate of change of rib cage circumference using a rib cage linear piezoelectric sensor, with said piezoelectric sensor being attached to an extensible rib cage belt by means of at least one non-electrically-conductive rivet, said linear piezoelectric sensor having an electrically-conductive coating on each side thereon, which coating on one side of said linear piezoelectric sensor is removed around said rivet, to provide an electric output;
   c. weighting and summing the outputs of the rib cage and abdominal sensors so that the summed output represents total respiratory flow.

2. The method according to claim 1, wherein said weighting step includes measuring the time average of the rib cage and abdominal rate of circumference change while the subject gently moves his abdomen in and out and thereafter adjusting the output of the properly summed signal to equal that of a previously calibrated pneumotachometer while the subject breathes normally.

3. The method according to claim 1, wherein said weighting step includes measuring the instantaneous rib cage and abdominal rate of circumference change while the subject breathes with rib cage and abdominal asynchrony through a pneumotachometer for 6–12 breaths and calibrating so that at the instant of zero respiratory flow the rib cage and abdominal signals are adjusted to be equal.

4. Apparatus for measuring respiratory air flow comprising:
   an extensible abdominal belt with a linear piezoelectric sensor attached thereto by means of at least one non-electrically-conductive rivet, said linear piezoelectric sensor having an electrically-conductive coating on each side thereon, which coating on one side of said linear piezoelectric sensor is removed around said rivet, for measuring the rate of change of abdomen circumference;

an extensible rib cage belt with a linear piezoelectric sensor attached thereto by means of at least one non-electrically-conductive rivet, said linear piezoelectric sensor having an electrically-conductive coating on each side thereon, which coating on one side of said linear piezoelectric sensor is removed around said rivet, said combined extensible rib cage belt and said linear piezoelectric sensor being adapted for measuring the rate of change of rib cage circumference; and means for weighting and then summing the outputs of the rib cage and abdominal sensors so that the summed output represents total respiratory flow.

5. The apparatus according to claim 4, in which said piezoelectric sensor is fastened to said belt by means of one or more plastic rivets and said coating on one side of said piezoelectric sensor is removed around each of said rivets.

6. The apparatus according to claim 4, wherein the sensor is permanently fastened to an extensible stretchable Velcro ® belt.

7. The apparatus according to claim 4, wherein the sensor is fastened by Velcro ® tabs to the extensible belts.

8. The apparatus according to claim 4, wherein several sensors are attached in series, around the extensible belts.

9. The apparatus according to claim 4, wherein the sensors are attached by Velcro ® tabs to a neoprene rubber vest.

* * * * *

UNITED STATES PATENT AND TRADEMARK OFFICE
CERTIFICATE OF CORRECTION

PATENT NO. : 4,960,118

DATED : October 2, 1990

INVENTOR(S) : Bernard E. Pennock

It is certified that error appears in the above-identified patent and that said Letters Patent is hereby corrected as shown below:

On the title page:
Under References Cited U.S. PATENT DOCUMENTS
"3,782,368  1/1974  Rebold  128/721" should read
--3,782,368  1/1974  Reibold  128/721--.

Column 5 Line 8 "$V_{RC}$ and $V_{AB}$" should read --$\dot{V}_{RC}$ and $\dot{V}_{AB}$--.

Claim 1 Line 24 Column 6 "on" should read --one--.

Signed and Sealed this

Twenty-fifth Day of June, 1991

*Attest:*

HARRY F. MANBECK, JR.

*Attesting Officer*   *Commissioner of Patents and Trademarks*